United States Patent [19]

Didriksen

[11] Patent Number: 4,600,577

[45] Date of Patent: Jul. 15, 1986

[54] PHARMACEUTICAL PREPARATIONS OF PINACIDAL

[75] Inventor: Erik J. Didriksen, Ballerup, Denmark

[73] Assignee: Leo Pharmaceutical Products Ltd. A/S (Lovens Kemiske Fabrik Produktionsaktieselkab), Ballerup, Denmark

[21] Appl. No.: 572,754

[22] Filed: Jan. 23, 1984

[30] Foreign Application Priority Data

Feb. 11, 1983 [DK] Denmark ................ 589/83

[51] Int. Cl.⁴ .................... A61K 9/14; A61K 9/54; A61K 9/58
[52] U.S. Cl. ........................ 424/20; 514/352; 514/353; 424/19; 424/37; 424/32; 424/33
[58] Field of Search ............. 514/349, 353, 352; 424/20, 37, 32, 33

[56]  References Cited

U.S. PATENT DOCUMENTS 4,057,636 11/1977 Peterson .................. 546/306
4,367,217 1/1983 Gruber et al. ............ 424/20

FOREIGN PATENT DOCUMENTS 2087235 5/1982 United Kingdom .

Primary Examiner—Donald B. Moyer
Assistant Examiner—C. Joseph Faraci
Attorney, Agent, or Firm—Cushman, Darby & Cushman

[57]  ABSTRACT

New pharmaceutical preparation containing pinacidil (N"-cyano-N-4-pyridyl-N'-1,2,2-trimethylpropylguanidine) in slow-release form, providing more uniform absorption rates and resulting blood levels when administered to the individual patients.

4 Claims, No Drawings

PHARMACEUTICAL PREPARATIONS OF PINACIDAL

The present invention relates to a new pharmaceutical preparation, more particularly a preparation containing pinacidil (N''-cyano-N-4-pyridyl-N'-1,2,2-trimethylpropylguanidine), and in particular a slow-release preparation containing pinacidil (as such or as nontoxic, pharmaceutically acceptable acid addition salt) as active ingredient, if desired together with one or more other therapeutically active ingredients. The present invention also relates to a method of producing said new pharmaceutical preparations and a method of treating patients suffering from e.g. hypertension using said new preparations.

Pinacidil, its preparation and use has been described, e.g. in U.S. Pat. No. 4,057,636.

Pinacidil has hitherto primarily been administered in the form of tablets, but due to pinacidil's solubility being largely pH-dependent (solubility in the almost neutral intestinal fluids only approximately one percent of its solubility in the acidic gastric fluids) the peak values obtained are highly influenced by the passage time of the tablet through the gastrointestinal tract, with resulting fluctuations in the blood pressure which is undesirable, together with a larger incidence of side effects.

The above U.S. Pat. No. 4,057,636 also proposes to administer the compounds described in form of sustained release tablets. However, when pinacidil is administered in slow-release tablets of the matrix-type, e.g. as described in British Pat. No. 1.137,156 or in tablets coated to delay the release of the contents, trials in human volunteers show a large variation in the individual absorption rates and resulting blood levels which makes the use of pinacidil rather unpredictable and therefore less attractive.

It has now been found that these drawbacks found with the known forms of administering pinacidil may be avoided by administering a mixture of at least two kinds of pellets containing pinacidil as one active ingredient, optionally together with other therapeutically active active ingredients and carriers and/or auxiliary agents, the kinds of pellets differing in permitting a release of their active contents at different pH-values, e.g. one part with rapid release in the stomach and slow release in the intestine, and one or more parts with no release in stomach and moderate release in the intestine.

According to the present invention this effect can be achieved by microencapsulating the active ingredients using a material which dissolves or is made permeable in the milieu in which it is desired to liberate the active ingredients. A further advantage is according to the present invention obtained when the microencapsulating material is chosen in such a way that release of the active components can only take place in the desired part of the gastro-intestinal tract. Thus it is avoided that an unintended quicker passage of an upper part of the gastro-intestinal tract could lead to a higher release than intended of the active components in the lower part of the tract.

A preferred method of achieving the above is by microencapsulating the first kind of pellets with a material which is dissolved or made permeable in the acidic milieu in the stomach, e.g. by using polymers synthesized from acrylic and methacrylic esters with a low content of quaternary ammonium groups (Eudragit ® RL) or polymers based on poly(meth)acrylic esters (Eudragit ® E30D), if desired with addition of hydrophilic film formers, such as polyethylene glycols or hydroxypropylmethylcellulose—or polymers synthesized from dimethylaminomethacrylate and other neutral methacrylic acid esters (Eudragit ® E).

Specifically useful are Eudragit ® RL and E, because they are not dissolved, but only made permeable in the neutral milieu in the intestines. Thus, if a pharmaceutical dosage unit containing a preparation according to the present invention should pass very quickly through the stomach, e.g. if it is administered on an empty stomach it will only give slight rise in the intended liberated amount of active component in the intestine.

The second kind of pellets is prepared by microencapsulating the active components with a polymer substance selected from the group consisting of anionic carboxylic polymers useful for pharmaceutical purposes and being difficultly soluble at a low pH but being soluble at a higher pH, the pH limit for solubility being in the interval of pH 5 to 7.5, said group comprising celluloseacetate phthalate (CAP) (5.0–5.5) hydroxypropylmethylcellulose phthalate (5.0–5.5), and methacrylic acid-methacrylic acid methyl ester polymers, such as Eudragit ® L (6.0) and Eudragit ® S (7.0). Numbers in brackets above are approximate pH dependent solubility limits above which the polymers become increasingly soluble. These polymers may be used alone or in combination with each other. The polymers may be admixed with plasticizers such as diethyl or dibutyl phthalates, citric acid esters, e.g. acetyltributyl phthalates, citric acid esters, e.g. acetyltributyl citrate (Citroflex ® A-4), glycerol fatty acid ester, e.g. glyceryl triacetate, stearic acid and fatty alcohols, such as cetanol and polyethylene glycols, such as macrogol. Suitably a polymer is selected which is insoluble or difficultly soluble in gastric juice, but soluble in intestinal juice. A preferred polymer is Eudragit ® S. Further preferred polymers are hydroxypropylmethylcellulose phthalate and Eudragit ® L, if desired in combination with Eudragit ® S.

The microencapsulated pellets can be prepared in the following manner.

First, pinacidil pellets are prepared by coating a carrier e.g. sugar/starch non pareils with a suspension of pinacidil.

For producing the first kind of pellets (the initial dose), an amount of the above pinacidil pellets are coated as described above, e.g. with an alcoholic solution of Eudragit ® RL, resulting in amount of coating constituting 2 to 10 percent, preferably approximately 4% of the weight of the pellets.

For producing the second kind of pellets (the depot- or repeat-dose), a further amount of the above pinacidil pellets are coated as described above, e.g. with an alcoholic solution of Eudragit ® S, resulting in an amount of coating constituting 5 to 20 percent, preferably approximately 12 percent of the weight of the pellets.

If desired, it is possible, by choosing suitable coating materials, to prepare further kinds of pellets from which the liberation of the active materials is further delayed, but usually it is sufficient to use the above described two kinds of pellets.

According to the invention, the above pellets are included in dosage units for administering to a patient in need of treatment.

By the term dosage unit is meant a unitary, i.e. a single dose which is capable of being administered to a patient, and which may be readily handled and packed, remaining as physically stable unit dose comprising a mixture of the above kinds of pellets as such or together with suitable pharmaceutically acceptable, non-toxic carriers and/or auxiliary agents, e.g. in the form of tablets, capsulae, etc.

For preparing the final dosage units, suitable amounts of the pellets constituting the initial dose and the repeat dose are mixed and preferably filled into capsules.

The ratio between the initial dose and the repeat dose may vary from 1:10 to 10:1 with the preferred ratio being approximately 1:5 and 5:1, in particular between 1:4 and 1:1.

The amount of the mixture of pellets is chosen with a view to the desired content of pinacidil in the final preparations.

Each dosage unit can contain about 10 to $10^6$ bodies. Preferably the number of bodies is about 200 to 1000. Thus each body of the preparation shall contain a fraction of a therapeutically effective dosage of the active component. The fraction can be $1.10^{-6}$ to $1.10^{-1}$ times such dosage and preferably $1.10^{-3}$ to $5.10^{-3}$ times such dosage. Among suitable dosage units capsules and tablets are specifically mentioned of which capsules are the most preferred embodiment. Pharmaceutically acceptable additives may be included in the dosage units together with the preparation of the invention. Preparations wherein the solid bodies are in admixture with or intended for mixing with a liquid medium are also within the scope of the invention.

As mentioned above, the mixture of the various kinds of pellets may be composed by varying proportions of the different types, thus enabling a variation in the time of onset of the antihypertensive effect and in the duration of said effect.

The present pharmaceutical preparations are advantageous in that they allow a less frequent regimen. With the conventional tablets hitherto used, a minimum of 4 times daily was necessary, and this could hardly be reduced further, even by using the usual slow-release preparations.

With the present preparations, it is possible to administer according to a three-times daily regimen, and in many cases, even a twice daily regimen can be practised. As non-compliance is a common cause of apparent failure of anti-hypertensive drug treatment, the present preparations represent a marked improvement.

As indicated above, the present preparations may contain further therapeutically active ingredients used in the treatment of hypertension, such as diuretics and-/or β-blocking agents, e.g. as described in the above U.S. Pat. No. 4,057,636.

The present preparations have shown to possess a good stability with a view to their shelf-life.

The preparations according to the invention will be further illustrated by the following Example.

EXAMPLE

| I. Preparation of Pinacidil pellets | |
| --- | --- |
| Pinacidil monohydrate | 50 g |
| Polysorbate 80 | 0.5 g |
| Water deionized | 100 ml |
| Silicone Antifoam M-30 emulstion | 1.5 g |

The suspension was ball-milled in a 600 ml glass bottle for minimum 2 hours using glass balls of 6 mm diameter. The particle size was controlled by microscopy and the milling was continued until most particles had a size less than 30 μm.

The suspension and glass balls were separated on a Buchner funnel (without filter paper). The balls were washed with 50 ml of deionized water, and the washings were added to the separated suspension which was then mixed with a solution of hydroxypropylmethylcellulose 6 cps (17 g) in deionized water (170 ml). The resulting suspension contained approximately 13 percent pinacidil monohydrate and 4 percent of hydroxypropylmethylcellulose.

Sugar/starch non pareils (333 g) were coated with the suspension thus prepared, using a fluid bed spray granulator.

| II. Coating of initial dose with Eudragit ® RL | |
| --- | --- |
| Eudragit ® RL | 16 g |
| was dissolved in | |
| Ethanol 99.9% | 250 ml |
| Water, deionized | 15 ml |
| Diethyl phthalate | 1.6 g |

Talc (4 g) was suspended in the spray liquid which with continuous stirring was applied onto pinacidil pellets (400 g) in a fluid bed spray granulator.

If desired, Eudragit ® E or Eudragit ® E30D could be substituted for Eudragit ® RL.

| III. Coating of repeat dose with Eudragit ® S | |
| --- | --- |
| Eudragit ® S | 50 g |
| was dissolved in | |
| Ethanol 99.9% | 800 ml |
| Water deionized | 40 ml |
| Diethyl phthalate | 5 g |

Talc (12.5 g) was suspended in the spray liquid which with continuous stirring was applied onto pinacidil pellets (400 g) in a fluid bed spray granulator.

IV. Mixing of initial dose and repeat dose

Pinacidil pellets as coated under II above (421.6 g) was mixed with pinacidil pellets as coated under III above (467.5 g) for 15 minutes in a cube tumbler, after a light dusting of the pellets with magnesium stearate.

The resulting mixture of pellets was filled into capsules, the size of which was chosen with view to the desired content of pinacidil monohydrate.

Thus, if the pinacidil content of the pellets was higher than 11 percent, a capsule size 2 could contain a dose corresponding to 25 mg of pinacidil monohydrate. If the pinacidil content of the pellets was higher than 8 percent, a capsule size 4 could contain a dose corresponding to 10 mg of pinacidil monohydrate.

What we claim is:

1. An improved antihypertensive composition in slow release form comprising an antihypertensive effective amount of N''-cyano-N-4-pyridyl-N'-1,2,2,trimethyl propylguanidine wherein the improvement comprises said propylguanidine being present in the form of a mixture of coated pellets, a portion thereof being:
   (a) rapid release pellets wherein the coating consists essentially of a copolymer of acrylic and methacrylic ester which releases the contents of the pellet at a pH<4, said coating being present in an amount from 2-10% by weight of the pellets; and
   (b) the remaining portion being coated pellets wherein the coating consists essentially of an anionic copolymer of methacrylic acid and methacrylic acid ester which releases the contents at a pH in the range of pH 5 to pH 7.5, said coating being present in an amount from 5–20% by weight of the pellets; and wherein the ratio of (a) to (b) is 1:10 to 10:1.

2. Pharmaceutical composition according to claim 1 in dosage unit form.

3. Pharmaceutical composition according to claim 2 in form of a capsule.

4. Method for treating patients suffering from hypertension comprising administering to said patients an effective amount of a composition according to claim 1.

* * * * *